(12) United States Patent
Williams et al.

(10) Patent No.: US 6,927,053 B2
(45) Date of Patent: *Aug. 9, 2005

(54) DUAL COMPONENT DENTAL COMPOSITION CONTAINING ENZYME

(75) Inventors: Malcolm Williams, Piscataway, NJ (US); Michael Prencipe, West Windsor, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 413 days.

This patent is subject to a terminal disclaimer.

(21) Appl. No.: 10/229,551

(22) Filed: Aug. 28, 2002

(65) Prior Publication Data

US 2004/0042977 A1 Mar. 4, 2004

(51) Int. Cl.⁷ ................................. C12N 9/34
(52) U.S. Cl. .............. 435/205; 435/201; 435/212; 435/219; 424/49; 424/50; 424/56; 424/94.1; 424/94.61; 424/94.65
(58) Field of Search .................. 435/205, 219, 435/212, 201; 424/94.1, 94.65, 94.61, 50, 56, 49

(56) References Cited

U.S. PATENT DOCUMENTS

| | | | |
|---|---|---|---|
| 4,986,981 A | 1/1991 | Glace et al. | 424/50 |
| 5,000,939 A * | 3/1991 | Dring et al. | 424/48 |
| 5,176,899 A * | 1/1993 | Montgomery | 424/50 |
| 6,652,841 B1 * | 11/2003 | Brown et al. | 424/49 |

FOREIGN PATENT DOCUMENTS

| | | | | |
|---|---|---|---|---|
| FR | 2345998 | 10/1977 | | A61K/7/28 |
| GB | 2160098 | 12/1985 | | A61K/7/28 |
| WO | 02089755 | 4/2002 | | A61K/7/16 |
| WO | 03094876 | 11/2003 | | A61K/7/16 |

OTHER PUBLICATIONS

Patent Abstracts of Japan: "Toiletry Product Blended with Enzyme"—Publication No. 01283213, dated Nov. 14, 1989.

Patent Abstracts of Japan: "Composition for Oral Cavity"—Publication No. 11322557, dated Nov. 24, 1999.

Patent Abstracts of Japan: "Dentifrice Composition"—Publication No. 2000360896, dated Jul. 5, 2002.

* cited by examiner

*Primary Examiner*—Leon B. Lankford, Jr.
(74) *Attorney, Agent, or Firm*—Kristyne A. Bullock

(57) ABSTRACT

A two component desensitizing dentifrice composition is disclosed which comprises a first dentifrice component containing an enzyme such as papain and a second dentifrice component containing an ionic surfactant such as sodium lauryl sulfate, the first and second dentifrice components being maintained separate from the other until dispensed for application to teeth whereby enzyme activity is maintained with improved dentifrice foaming characteristics.

15 Claims, No Drawings

DUAL COMPONENT DENTAL COMPOSITION CONTAINING ENZYME

BACKGROUND OF THE INVENTION

1. Field of the Invention

This invention relates generally to oral compositions for enhancing oral hygiene, and more particularly, to enzyme containing dual component compositions for enhancing oral hygiene.

2. The Prior Art

Oral compositions such as toothpastes, gels and mouth washes are designed to loosen and remove plaque in conjunction with a regular toothbrushing regimen. Dental plaque is present to some degree, in the form of a film, on virtually all dental surfaces. It is a byproduct of microbial growth, and comprises a dense microbial layer consisting of a mass of microorganisms embedded in a polysaccharide matrix. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The problem associated with the formation of plaque on the teeth lies in the tendency of plaque to build up and eventually produce gingivitis, periodontitis and other types of periodontal disease, as well as dental caries and dental calculus.

It is known to the art to incorporate antimicrobial agents in oral compositions wherein these agents destroy or inhibit oral bacteria. Other agents are also incorporated in the oral composition to enhance the efficacy of the antimicrobial agents. For example, it is known to incorporate enzymes in oral compositions which disrupt or interfere with plaque formation and bacterial adhesion to tooth surfaces as disclosed in U.S. Pat. Nos. 2,527,686; 3,991,177; 3,194,738; 4,082,841; 4,115,546; 4,140,759; 4,152,418; 4,986,981; 5,000,939; 5,370,831; 5,431,903; 5,537,856; 5,849,271.

A problem encountered with the use of enzymes in oral care compositions is that often the enzyme of choice is not compatible with surfactants, namely ionic surfactants such as anionic surfactants which are preferred for use in oral compositions such as dentifrices and mouthwashes to achieve increased prophylactic action, provide superior foaming properties and render the compositions more cosmetically acceptable. Anionic surfactants such as the higher alkyl sulfates are not compatible with enzymes as the surfactant facilitates denaturing of the enzyme and loss in activity. As a result, the use of this desirable class of surfactants has been avoided by the art in the preparation of enzyme containing dentifrices.

SUMMARY OF THE INVENTION

The present invention is based upon the discovery that when a dual component dentifrice comprised of separately housed dentifrice components in which a first component contains an ionic or other surfactant normally incompatible with an enzyme and the second component contains the enzyme, when the components are mixed and combined during use, the enzyme is not found to denature but retains its activity in the presence of the normally incompatible ionic surfactant for at least the period of time involved in toothbrushing.

In accordance with the present invention there is provided a method for combining the plaque dispersion properties of active enzymes and the superior foaming action of ionic surfactants using a multicomponent dentifrice which dentifrice is comprised of separately housed, semi-solid aqueous components; the first component containing the enzyme in an orally acceptable vehicle and a second component containing an ionic surfactant in an orally acceptable vehicle whereupon combination of the components provides a dentifrice having superior foaming properties without antiplaque enzyme activity being significantly affected.

DESCRIPTION OF THE PREFERRED EMBODIMENTS

In use, the components of the two component dentifrice of the present invention comprise a first enzyme containing dentifrice component, and a second ionic surfactant containing dentifrice component. The two components are preferably combined for use in approximately equal weight proportions, so that about one-half of the concentration of any particular ingredient within either component will be present when the components are combined and applied to the teeth, as by brushing. Both components are preferably formulated to have similar physical characteristics, so that the two components may be simultaneously delivered in the desired predetermined amounts by extrusion when separately housed in a multicompartmented tube or pump device.

First Dentifrice Component

Enzymes

The enzymes useful in the practice of the present invention include enzymes extracted from natural fruit products such as well-known protein substances within the class of proteases, which breakdown or hydrolyze proteins. The proteolytic enzymes are obtained from natural sources or by the action of microorganisms having a nitrogen source and a carbon source. Examples of proteolylic enzymes useful in the practice of the present invention include the naturally occurring enzymes papain (from papaya), bromelain (from pineapple), as well as serine proteases such as chymotrypsin. Additional enzymes include ficin and alcalase.

Enzymes such as proteolytic enzymes are included in the first dentifrice component of the present invention at a concentration of about 0.010 to about 10.0% by weight and preferably about 0.2 to about 5% by weight.

Papain obtained from the milky latex of the Papaya tree is the proteolytic enzyme preferred for use in the practice of the present invention and is preferably incorporated in the oral care composition of the present invention in an amount of about 0.2 to about 5% by weight, such papain having an activity of 150 to 900 units per milligram as determined by the Milk Clot Assay Test of the Biddle Sawyer Group (see J. Biol. Chem., vol. 121, pages 737–745).

Enzymes which may beneficially be used in combination with the proteolytic enzymes include carbohydrases such as glucoamylase, alpha-amylase, beta-amylase, dextranase and mutanase, tannase and lipases such as plant lipase, gastric lipase and pancreatic lipase.

Glucoamylase is a saccharifying glucoamylase of *Aspergillus niger* origin. This enzyme can hydrolyze both the alpha-D-1,6 glucosidic branch points and the alpha-1,4 glucosidic bonds of glucosyl oligosaccharides. The product of this invention comprises about 0.01 to 10% of the carbohydrases. The lipase enzyme is derived from a select strain of *Aspergillus niger*. The enzyme has maximum lipolytic activity at pH 5.0 to 7.0 when assayed with olive oil. The enzyme has 120,000 lipase units per gram. Among the carbohydrases useful in accordance with this invention are glucoamylase, alpha and beta-amylase, dextranase and mutanase.

Other enzymes which may be denatured in the presence of anionic surfactants and used in the practice of the present invention include other carbohydrases such as alpha-amylase, beta-amylase, dextranase and mutanase and lipases such as plant lipase, gastric lipase, pancreatic lipase, pectinase, tannase lysozyme and serine proteases.

The lipase enzyme is derived from a select strain of *Aspergillus niger*, exhibiting random cleaving of the 1,3 positions of fats and oils. The enzyme has maximum lipolytic activity at pH 5.0 to 7.0 when assayed with olive oil. The enzyme has a measured activity of 120,000 lipase units per gram. The lipase may be included in the dentifrice composition at a concentration of about 0.010 to about 5.0% by weight and preferably about 0.02 to about 0.10% by weight.

The presence of tannase enzyme can be further beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Other suitable enzymes which can comprise the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, these two corbohydrates are polymerized to form the cell wall polysaccharide. Additionally, pectinase, an enzyme that is present in most plants facilitates the hydorlysis of the polysaccharide pectin into sugars and galacturonic acid. Finally, glucanase, which may be utilized to catalyze the breakdown of complex carbohydrates to glucans and the hydrolysis of beta glucan to glucose.

Enzyme Stabilizing Agents

The enzyme containing component of the present invention may also contain ingredients which stabilize enzymes in a dentifrice environment. These stabilizers protect the enzyme from inactivation by chelating metal impurities present in the oral composition which have the propensity to denature the active site of the enzyme by protecting the enzyme from oxidation. Agents stabilizing the enzyme against oxidation include sodium bisulfite, metal gallates, sodium stannate, 3,5,-di-tert-butyl-4-hydroxytoluene (BHT), Vitamin E ($\alpha$, $\beta$, $\gamma$, forms)/Vitamin E acetate and ascorbic acid at concentrations between about 0.03 to about 1.5%, preferably between about 0.3 and about 0.75%.

Additional chelating agents of mono and di charged cationic species include sodium tripolyphosphate and tetrasodium pyrophosphate, ethylene diamine tetraacetic acid and sodium gluconate which may be incorporated in the dentifrice component at a concentration of about 0.01 to about 1% by weight and preferably between about 0.1 to about 0.5% by weight.

Dentifrice Vehicle

Orally-acceptable vehicles used to prepare the dentifrice components of the present invention include a water-phase, containing a humectant therein. The humectant is preferably glycerin, sorbitol, xylitol, and/or propylene glycol of molecular weight in the range of 200 to 1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 25 to 70% by weight of the dentifrice component. Water employed in the preparation of commercially suitable oral compositions should preferably be deionized and free of organic impurities. These amounts of water include the free water which is added plus that which is introduced with other materials such as with sorbitol.

Nonionic Surfactants

Nonionic surfactants compatible with enzymes present in the first dentifrice component include nonanionic polyoxyethylene surfactants such as Polyoxamer 407, Steareth 30, Polysorbate 20, and PEG-40 castor oil and amphoteric surfactants such as cocamiopropyl betaine (tegobaine) and cocamidopropyl betaine lauryl glucoside condensation products of ethylene oxide with various hydrogen containing compounds that are reactive therewith and have long hydorphobic chains (e.g., aliphatic chains of about 12 to 20 carbon atoms), which condensation products ("ethoxamers") contain hydrophilic polyoxyehtylene moieties, such as condensation products of poly (ethylene oxide) with fatty acids, fatty alcohols, fatty amides and other fatty moieties, and with propylene oxide and polypropylene oxides (e.g., Pluronic®materials). The nonionic surfactants are included in the oral composition at a concentration of between about 2 to abut 10% by weight and preferably between about 3.5 to 6.5% by weight.

Abrasives

In the preparation of dentifrice components of the present invention abrasives which may be used to prepare the components of the present invention include silica abrasives such as precipitated silicas having a mean particle size of up to about 20 microns, such as Zeodent 115, marketed by J. M. Huber Chemicals Division, Havre de Grace, Md. 21078, or Sylodent 783 marketed by Davison Chemical Division of W. R. Grace & Company. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Preferred abrasive materials useful in the practice of the preparation of the dentifrice components in accordance with the present invention include silica gels and precipitated amorphous silica having an oil absorption value of less than 100 cc/100 g silica and preferably in the range of from about 45 cc/100 g to less than about 70 cc/ 100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Oil absorption values are measured using the ASTM Rub-Out Method D281. The low oil absorption silica abrasive is present in the oral are compositions of the present invention at a concentration of about 5 to about 40% by weight and preferably about 10 to about 30% by weight.

Low oil absorption silica abrasives particularly useful in the practice of the present invention are marketed under the trade designation Sylodent XWA by Davison Chemical Division of W. R. Grace & Co., Baltimore, Md. 21203. Sylodent 650 XWA, a silica hydrogel composed of particles of colloidal silica having a water content of 29% by weight averaging from about 7 to about 10 microns in diameter, and an oil absorption of less than 70 cc/100 g of silica is a preferred example of a low oil absorption silica abrasive useful in the practice of the present invention.

The dentifrice components of the present invention can contain a variety of optional ingredients. As described below, such optional ingredients can include, but are not limited to, thickening agents, a source of fluoride ions, a flavoring agent, antibacterial agents, antitartar and coloring agents.

Thickening Agents

Thickeners used in the preparation of the dentifrice components of the present invention include natural and synthetic gums and colloids. Not all naturally occurring polymer thickeners (such as cellulose or carrageenans) are compatible with enzymes. Thickeners compatible with enzymes such as proteolytic enzymes, include xanthan gum, polyglycols of varying molecular weights sold under the tradename Polyox and polyethylene glycol. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays, lithium magnesium silicate (Laponite)and magnesium aluminum silicate (Veegum).

The thickening agent is present in the dentifrice composition in amounts of about 0.1 to about 10% by weight, preferably about 0.5 to about 4.0% by weight.

Fluoride and Other Active Agents

The oral composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, sodium monfluorophosphate (MFP), ammonium fluorosilicate, as well as tin fluorides, such as stannous fluoride and stannous chloride. Sodium fluoride or MFP is preferred.

In addition to fluoride compounds, there may also be included in the oral compositions of the present inventions antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, polyphosphates such as sodium tripolyphosphate, sodium hexametaphosphate and cyclic phosphates such as sodium tripolyphosphate sodium trimetaphosphate. These antitartar agents are included in the dentifrice composition at a concentration of about 1 to about 5% by weight.

Another active agent useful in dentifrice compositions of the present invention are antibacterial agents, which can be from 0.2 to 1.0% by weight of the dentifrice composition. Such useful antibacterial agents include non-cationic antibacterial agents which are based on phenolic or bisphenolic compounds, such as halogenated diphenyl ethers such as Triclosan (2,4,4'-trichloro-2'-hydroxydiphenyl ether).

Flavor

The dentifrice components of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the oral composition at a concentration of about 0.1 to about 5% by weight and preferably about 0.5 to about 1.5% by weight.

Other Ingredients

Various other materials may be incorporated in the dentifrice components of the present invention, including desensitizers, such as potassium nitrate; whitening agents, such as hydrogen peroxide, calcium peroxide and urea peroxide; preservatives; silicones; and chlorophyll compounds. These additives, when present, are incorporated in the dentifrice components of the present invention in amounts which do not substantially adversely affect the properties and characteristics desired.

Second Dentifrice Component

The vehicle of the second dentifrice component is formulated to have a composition similar to the vehicle of the first dentifrice component, so that two components will be of substantially equivalent rheologies, which will permit them to be synchronously coextrudable from a container in which the components are separately housed. In order to maintain that the physical characteristics of the second component have rheological properties substantially equivalent to the first component, the vehicle composition of the second component, specifically the humectant and abrasive content, is adjusted.

The water and humectant comprise the liquid portion of the second dentifrice component. The humectant is preferably sorbitol, but other humectants such as glycerin and polyethylene glycol may also be employed. The humectant content is generally in the range of about 30% to about 70% by weight and preferably about 40 to about 65% by weight. the water content is in the range of about 5 to about 40% by weight and preferably 10 to about 30% by weight.

Preferred abrasives are siliceous materials, such as silica, and preferably a precipitated amorphous hydrated silica, and preferably a precipitated amorphous hydrated silica, such as Zeodent 115, available from Huber Corporation. The abrasive is generally present in the second dentifrice component at a concentration of about 10 to about 40% by weight and preferably about 15 to about 30% by weight.

Ionic Surfactants

Ionic surfactants incorporated in the second dentifrice component are preferably anionic surfactants, examples of which include higher alkyl sulfates such as potassium or sodium lauryl sulfate which is preferred, higher fatty acid monoglyceride monosulfates, such as the salt of the monosulfatedmonoglyceride of hydrogenated coconut oil fatty acids, alkyl aryl sulfoantes such as sodium dodecyl benzene sulfonate, higher fatty sulfoacetates, higher fatty acid esters of dihydorxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine and the salts of N-lauroyl, N-myristoyl, or N-palmitoyl sarcosine. The surfactant is generally present in the potassium salt dentifrice compositions of the present invention at a concentration of about 0.5 to about 5.0% by weight.

A thickener may be incorporated in the second dentifrice component at a concentration of about 0.5 to abut 10% by weight and preferably about 1 to about 5% by weight. Organic thickeners of natural and synthetic gums of the same type used to prepare the dentifrice component may also be incorporated at a concentration of about 0.1 to abut 3% by weight and preferably about 0.2 to about 2% by weight.

Additional ingredients such as fluoride and other active agents such as antitartar agents, flavors and sweeteners similar to that used for the preparation of the first component may be included in the preparation of the second dentifrice component at similar concentrations.

Preparation of Dentifrice Components

To prepare the enzyme containing dentifrice component of the present invention, generally the humectants such as glycerin, sorbitol are dispersed in the water in a conventional mixer under agitation. Into the dispersion are added salts, such as sodium fluoride anticaries agents, chelating agents such as bisulfite salts, antitartar agents such as tetrasodium pyrophosphate and sodium tripolyphosphate and any sweeteners; the resultant mixture is agitated until a homogeneous gel phase is formed. Into the gel phase are added a pigment such as $TiO_2$, and any buffering salt such as $NaH2PO_4$ Na2HPO4 to buffer the pH at 6.3 to 7.5. These ingredients are mixed until a homogenous phase is obtained. Thereafter a dispersion in water and humectant of enzyme compounds such as papain, glycoamylase is added and admixed with the homogeneous phase This mixture is then transferred to a high speed/vacuum mixer; wherein, thickeners such as xanthan gum, Zeodent 165, laponite ingredients are added to the mixture. Thereafter the abrasive is added together with the flavor oils to be included in the composition and the solution is added along with the nonionic surfactants to the mixture, which is then mixed at high speed for from 5 to 30 minutes, under vacuum of from about 20 to 50 mm of Hg, preferably about 30 mm Hg. The resultant product is in each case is a homogeneous, semi-solid, extrudable paste or gel product. The final pH of the dentifrice measured neat was determined to range between 6.7 and 7.25.

To prepare the second dentifrice components of the present invention, generally the humectants, for example, sorbitol are dispersed with any organic thickeners and sweetener. Water is then added into this dispersion and the ingredients mixed until a homogenous phase is obtained for the component. Thereafter silica abrasive, flavor and ionic surfactant ingredients are added and the ingredients mixed at high speed under vacuum of from about 20 to 100 mm of Hg. The resultant product, in the case of each component, is a homogeneous, semi-solid, extrudable paste product.

The multicomponent dentifrice composition of the present invention is packaged in a suitable dispensing container in which the components are maintained physically separated and from which the separated components may be dispensed synchronously as a combined ribbon for application to a toothbrush. Such containers are known in the art. An example of such a container is a two compartment dispensing container, such as a pump or a tube, having collapsible sidewalls, as disclosed in U.S. Pat. Nos. 4,487,757 and 4,687,663; wherein, the tube body is formed from a collapsible plastic web such as polyethylene or polypropylene and is provided with a partition within the container body defining separate compartments in which the physically separated components are stored and from which they are dispensed through a suitable dispensing outlet.

The following example is further illustrative of the present invention, but it is understood that the invention is not limited thereto. All amounts and proportions referred to herein and in the appended claims are by weight, unless otherwise stated.

EXAMPLE

A two component (Component A and B) enzyme containing dentifrice of the present invention was prepared, wherein Component A was a paste prepared with the enzymes papain and glycoamylase and the second Component B was prepared having incorporated therein the anionic surfactant sodium lauryl sulfate. The ingredients of Components A and B are listed in Table I below.

TABLE I

| Ingredient | Component A Wt. % | Ingredient | Component B Wt. % |
|---|---|---|---|
| Water | 16.0 | Water | 9.8 |
| Pluronic F-127 | 1.50 | Carboxymethyl cellulose | 0.60 |
| Laponite D | 0.70 | Tetrasodium pyrophosphate | 0.50 |
| Glycerin | 18.13 | NaFluoride | 0.243 |
| Tetrasodium pyrophosphate | 2.0 | Sorbitol | 59.937 |
| Sodium tripolyphosphate | 3.0 | NaSaccarin | 0.30 |
| Xanthan | 0.35 | Silica | 25.50 |
| NaFluoride | 0.243 | Flavor | 0.72 |
| NaSaccarin | 0.4 | Sodium lauryl sulfate (SLS) | 2.40 |
| NaH2PO4 | 0.03 | | |
| Na2HPO4 | 0.2 | | |
| NaHSO3 | 0.1 | | |
| Sorbitol | 20.0 | | |
| Sylodent XWA 650 | 20.0 | | |
| Zeodent 115 | 5.0 | | |
| Zeodent 165 | 1.75 | | |
| TiO2 | 0.4 | | |
| PEG-600 | 4.0 | | |
| Papain | 1.0 | | |
| Glucoamylase | 0.1 | | |
| Flavor | 1.1 | | |
| Polysorbate | 2.0 | | |
| Tegobetaine | 2.0 | | |

To determine the stability of enzyme (papain) activity of the dentifrice when the individual components (Components A and B) are mixed and combined in tooth brushing, equal amounts (3 grams) of Components A and B were mixed in 18 milliliters of water and stirred for 3, 10 and 20 minute intervals. Time expended by consumers involved in toothbrushing normally ranges from 0.5 to 2.0 minutes.

The protease enzyme activity for each solution was determined using a standard enzyme assay procedure, namely a procedure developed by Sigma Chem. Corp using a titrimetric determination of the acid produced during the hydrolysis of benzoyl-L-arganinine ethyl ester (BAEE); (Amon, R., Methods in Enzymology, 1970).

A similar enzyme activity assay was conducted for Component A alone. The results of the assays are recorded in Table II below.

TABLE II

| | Papain Activity % Enzyme Activity Remaining | | |
|---|---|---|---|
| | Mixing Time: | | |
| Component | 3 minutes | 10 minutes | 20 minutes |
| A | 100% | 100% | 97% |
| A + B | 96% | 82% | 43% |

The results recorded in Table II show that both dentifrice systems had similar enzyme activities in the first few minutes of mixing. However, the combined components (A+B) started to lose enzyme activity after 10 minutes of mixing. The results in Table II show that unexpectedly, the enzyme can coexist in the presence of the anionic surfactant SLS for a period of time sufficient (3 minutes) to provide activity and plaque dispersion efficacy, before a significant enzyme denaturation is encountered.

The foam characteristics of Component A and the mixture of Components A and B were also evaluated. The foam volume measurements were made by dispersing 10 grams of dentifrice in 90 milliliters (ml) of distilled water. Then 20 ml of the slurry was transferred into a 50 ml graduated cylinder. The foam was generated by alternately inverting the cylinder (shaking) 10 times. The foam volume was monitored as a function of time using the graduation mark.

The result of the foam tests are recorded in Table III below. For purposes of comparison, a commercially available silica based fluoride toothpaste which did not contain enzymes (Colgate ®Cavity Protection) but which contained sodium lauryl sulfate as the surfactant was also evaluated for foam volume.

TABLE III

FOAM PROPERTIES

| Dentifrice Component | Foam Volume, ml |
| --- | --- |
| A | 42 |
| (A + B) | 64 |
| Colgate ® Cavity Protection | 67 |

The results recorded in Table III show that the dentifrice composed of combined dentifrice Components A and B delivered foam substantially greater than the enzyme containing Component A. Further, the combined dentifrice components (A+B) delivered foam substantially equivalent to silica based commercial toothpastes which contained sodium lauryl sulfate.

What is claimed is:

1. A two component enzyme dentifrice composition having foaming characteristics which comprises a first dentifrice component containing an enzyme in an orally acceptable vehicle which is substantially free of ionic surfactant and a second dentifrice component containing an ionic surfactant in an orally acceptable vehicle which is substantially free of enzyme, the first and second components being maintained separate from each other until dispensed and combined for application to teeth, whereby enzyme activity is substantially retained during application of the combined components to teeth during brushing.

2. The composition of claim 1 wherein the enzyme is papain.

3. The composition of claim 1 wherein the enzyme is glucoamylase.

4. The composition of claim 1 wherein the ionic surfactant is anionic surfactant.

5. The composition of claim 4 wherein the anionic surfactant is sodium lauryl sulfate.

6. The composition of claim 1 wherein the enzyme is present in the first dentifrice component at a concentration of about 0.01 to about 10% by weight.

7. The composition of claim 1 wherein the ionic surfactant is present in the second component at a concentration of about 1 to about 5% by weight.

8. A method for improving the foam characteristics of an oral care composition containing enzymes without substantial denaturation of the enzyme which comprises preparing (1) a first dentifrice component containing the enzyme in an orally acceptable vehicle which is substantially free of ionic surfactant and (2) a second dentifrice component containing an ionic surfactant in an orally acceptable vehicle which is substantially free of enzyme, separately housing the first and second components, dispensing the first and second components simultaneously, combining the dispensed components and thereafter applying the combined components to the teeth whereby the enzyme activity is substantially retained during application to the teeth.

9. The method of claim 8 wherein the ionic surfactant is an anionic surfactant.

10. The method of claim 9 wherein the anionic surfactant is sodium lauryl sulfate.

11. The method of claim 8 wherein the enzyme is papain.

12. The method of claim 8 wherein the enzyme is glucoamylase.

13. The method of claim 8 wherein the enzyme is present in the dentifrice component at a concentration of about 0.01 to about 10% by weight.

14. The method of claim 7 wherein the ionic surfactant is present in the dentifrice component at a concentration of about 1 to about 5% by weight.

15. The method of claim 8 wherein the first and second components are housed in a common container and are separated from one another by a wall integrally formed with the container which prevents mixing of the components prior to being dispensed.

* * * * *